(12) United States Patent
Sjunnesson et al.

(10) Patent No.: US 10,973,498 B2
(45) Date of Patent: Apr. 13, 2021

(54) BIOPSY KIT AND METHOD OF REMOVAL OF A PIECE OF TARGET TISSUE

(71) Applicant: Novoaim AB, Stockholm (SE)

(72) Inventors: Håkan Sjunnesson, Stockholm (SE); Per Hedén, Stockholm (SE)

(73) Assignee: Resitu Medical AB, Stockholm (SE)

( * ) Notice: Subject to any disclaimer, the term of this patent is extended or adjusted under 35 U.S.C. 154(b) by 467 days.

(21) Appl. No.: 15/516,132

(22) PCT Filed: Sep. 28, 2015

(86) PCT No.: PCT/SE2015/051016
§ 371 (c)(1),
(2) Date: Mar. 31, 2017

(87) PCT Pub. No.: WO2016/053165
PCT Pub. Date: Apr. 7, 2016

(65) Prior Publication Data
US 2017/0303902 A1     Oct. 26, 2017

(30) Foreign Application Priority Data

Oct. 3, 2014  (SE) ..................................... 1451173-7

(51) Int. Cl.
*A61B 10/02* (2006.01)
*A61B 18/14* (2006.01)
(Continued)

(52) U.S. Cl.
CPC ...... *A61B 10/0233* (2013.01); *A61B 10/0266* (2013.01); *A61B 10/0275* (2013.01);
(Continued)

(58) Field of Classification Search
CPC ............ A61B 10/0233; A61B 10/0266; A61B 10/0275; A61B 10/0283; A61B 18/1477
See application file for complete search history.

(56) References Cited

U.S. PATENT DOCUMENTS

| 4,461,305 A | 7/1984 | Cibley |
| 5,353,804 A * | 10/1994 | Kornberg ........... A61B 10/0266 |
| | | 600/567 |

(Continued)

FOREIGN PATENT DOCUMENTS

| CN | 101502426 A | 8/2009 |
| WO | WO 95/13752 A1 | 5/1995 |
| WO | WO 00/56220 A1 | 9/2000 |

*Primary Examiner* — Devin B Henson
(74) *Attorney, Agent, or Firm* — Blank Rome LLP

(57) ABSTRACT

A biopsy kit, comprising a penetration rod having a distal end portion, a cutting tube enclosing the penetration rod, comprising circumventing cutting means. The cutting tube is extendable from the penetration rod for cutting and enclosing a piece of target tissue, and a cutting device is extendable from the penetration rod and comprises distal cutting means for cutting off the piece of target tissue from the body. A method: penetrating tissue using a penetration rod; upon reaching the tissue to be removed, carrying out the following two steps in any consecutive order: extending a cutting device from the penetration rod to penetrate the target tissue, extending a cutting tube to cut out and enclose the target tissue; and additionally cutting off the piece of target tissue using a cutting means of the cutting device after extending the cutting device either before or after extending the cutting tube.

14 Claims, 1 Drawing Sheet

(51) Int. Cl.
*A61B 10/00* (2006.01)
*A61B 18/00* (2006.01)

(52) U.S. Cl.
CPC .......... *A61B 18/1477* (2013.01); *A61B 10/00* (2013.01); *A61B 10/0283* (2013.01); *A61B 18/00* (2013.01)

(56) References Cited

U.S. PATENT DOCUMENTS

| | | | |
|---|---|---|---|
| 5,431,635 A * | 7/1995 | Yoon | A61B 10/0233 604/164.12 |
| 5,486,161 A * | 1/1996 | Lax | A61B 10/0233 604/22 |
| 6,136,014 A | 10/2000 | Sirimanne et al. | |
| 2003/0023239 A1 | 1/2003 | Burbank et al. | |
| 2005/0054948 A1* | 3/2005 | Goldenberg | A61B 10/025 600/567 |
| 2008/0119846 A1* | 5/2008 | Rioux | A61B 18/1477 606/41 |
| 2009/0112119 A1 | 4/2009 | Kim | |
| 2009/0131819 A1 | 5/2009 | Ritchie et al. | |
| 2009/0227895 A1 | 9/2009 | Goldenberg | |

* cited by examiner

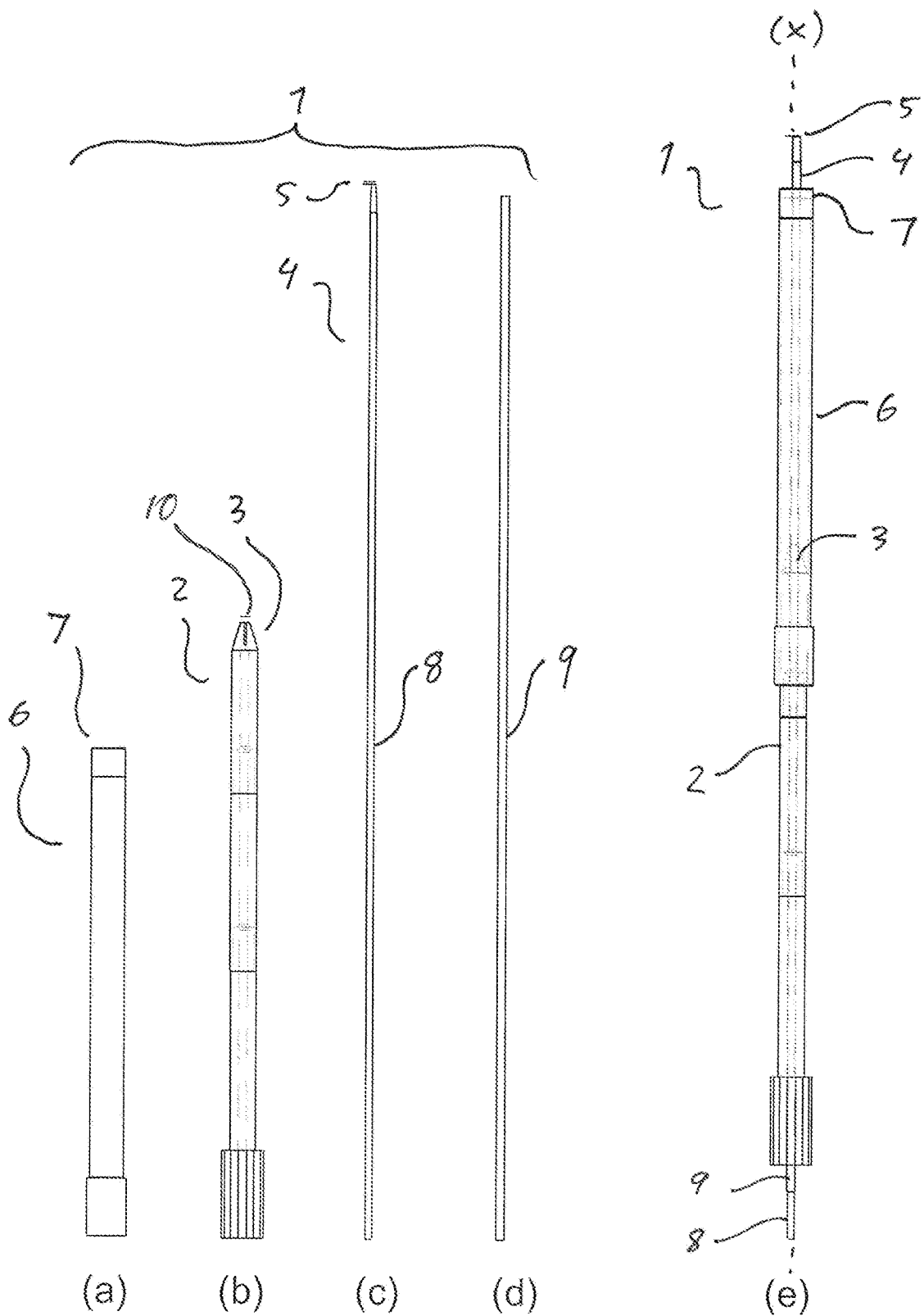

BIOPSY KIT AND METHOD OF REMOVAL OF A PIECE OF TARGET TISSUE

TECHNICAL FIELD

The present invention relates generally to a biopsy kit and a method of removal of a piece of target tissue.

BACKGROUND ART

In prior art biopsy instruments are known which are either fine needle biopsy instruments which are easy to use and low cost but the results are not always reliable or very complicated and expensive and usually used in systems like stereotactic systems.

SUMMARY OF INVENTION

With the present biopsy kit and method of removal of a piece of target tissue a fast and efficient technique for removing pieces of target tissue, for example core biopsies, specifically from deeply situated target areas is provided. It also provides a minimally invasive technique with minimal scaring, minimal bleeding and minimal injuries to surrounding tissue and nerves and only extracting target tissue.

The present technique enables high precision core biopsies to be performed manually, possibly by one hand only, and it is ideal to use with high quality imaging systems, for example state of the art ultrasound. It is simple, safe and fast procedure compared to other core biopsy methods. The kit is a low cost instrument compared to previously used instruments and is preferably disposable, which allows safe and guarantied sterilization, ready to use and simple distribution and handling. By having kits of varying sizes, length and/or diameter, a suitable kit can be chosen for each surgery/biopsy. It is also possible to use as a kit and a method for surgery with all the above advantages.

An object of the present invention is to provide a cost effective biopsy kit. Another object of the present invention is to provide a biopsy kit, which is easy to handle. Additionally, it is an object to provide a safe biopsy kit and to provide the possibility to totally remove tumors en bloc.

In order to try to fulfill the objects, a biopsy kit is provided comprising a penetration rod having a distal end portion for penetration into the body, a cutting tube enclosing the penetration rod, comprising circumventing cutting means, the cutting tube being extendable from the distal end portion of the penetration rod for cutting and enclosing the piece of target tissue, and a cutting device extendable from the penetration rod and comprising distal cutting means for cutting off the piece of target tissue from the body.

Preferably the distal end portion of the penetration rod is blunt.

With such a kit having a blunt penetration rod it is possible to penetrate all the way into the position before the target area or biopsy position without cutting tissue. Instead the penetration rod will separate the tissue while penetrating the body. Thus, bleeding and the risk of injuries to nerves, blood vessels and surrounding tissue will be minimized. The present kit is also possible to use manually without the need of stereotactic systems, although it is of course possible to arrange the present instrument in such a system.

According to one embodiment, the penetration rod, cutting device and the cutting tube are arranged coaxially along an axis.

According to another embodiment, the cutting device is rotatable around the axis and the cutting means extend radially from the axis.

According to one embodiment, the cutting device is extendable from the penetration rod in an axial direction. The cutting device may take a first position where the cutting device is protected by the penetration rod, a second position where the cutting means (5) extends just enough to be able to cut tissue at the distal end portion (3) of the penetration rod (2) or a third position where the cutting means (5) extends through the piece of target tissue in order to be able to cut off the piece of target tissue. In the second position it is possible to cut during the penetration on its way to the target area. For example, if the penetration rod needs to get through harder tissue.

Preferably the cutting means of the cutting device is an electrode for diathermy. In such an embodiment it is preferred that the cutting device comprises an electrical connector for the electrode. It is also preferable to protect the electrical connector by insulating means. The advantage of having diathermy electrodes is that there will be no or minimized bleeding during cutting in the tissue.

According to one embodiment, a sealing means is provided between the penetration rod and the cutting tube and/or between the penetration rod and the cutting device. Thus it is possible to provide vacuum in the distal end of the biopsy kit.

As previously mentioned a negative pressure or vacuum is possible to provide during use by means of axial movement of the penetration rod. Due to the vacuum a more secure taking of the biopsy is provided and additionally a less risk of losing the taken biopsy material during withdrawal of the instrument is provided. The vacuum also facilitates the cutting of the target tissue by pulling the tissue into the container. A negative pressure may also be applied from an external source. The negative pressure may also be used for evacuating blood or other fluids.

In a further embodiment a second tube is arranged concentrically outside the cutting tube. In this way it is possible to minimize the risk of seeding tumor cells in the penetration channel, which is made by the biopsy kit, during withdrawal of the biopsy kit by means of keeping the second tube in the penetration channel during the withdrawal of the biopsy kit. Thereafter the second tube can be removed from the body.

Preferably, the biopsy instrument is operable with only one hand.

A method of removal of a piece of target tissue from a body is also provided. The method comprises the steps
  penetrating tissue of the body using a penetration rod,
  upon reaching the piece of target tissue to be removed, carrying out the following two steps in any consecutive order,
  extending a cutting device from the penetration rod to penetrate the piece of target tissue,
  extending a cutting tube from the penetration rod to cut out and enclose the piece of target tissue,
and additionally
  cutting off the piece of target tissue using a cutting means of the cutting device after extending the cutting device either before or after extending the cutting tube.

The method uses diathermy connected to the cutting means (5) of the cutting device in one embodiment.

According to another embodiment the method provides negative pressure to the biopsy kit.

According to a further embodiment the method comprises extending the cutting device from the penetration rod from a first position, where the cutting means is protected by the penetration rod, to a second position where the cutting means extends just enough to be able to cut tissue at the distal end portion of the penetration rod, and cutting tissue with the cutting means in the second position.

BRIEF DESCRIPTION OF DRAWINGS

The invention is now described, by way of example, with reference to the accompanying drawings, in which:
FIG. 1a shows one embodiment of a cutting tube,
FIG. 1b shows one embodiment of a penetration rod,
FIG. 1c shows one embodiment of a cutting device,
FIG. 1d shows one embodiment of insulating means, and
FIG. 1e shows one embodiment of a kit assembled.

DESCRIPTION OF EMBODIMENTS

In the following, a biopsy kit 1 in different embodiments and a method for taking a biopsy are described.

A biopsy kit 1 for removal of a piece of target tissue from a body is provided comprising at least a penetration rod 2, preferably having a blunt distal end 3, a cutting device 4 and a cutting tube 6. In FIG. 1a a cutting tube 6 is shown and the cutting tube has a distal circumventing cutting edge 7. The cutting tube 6 is enclosing a penetration rod 2, see FIG. 1b, and is axially extendable from the distal end portion 3 of the penetration rod 2 in a distal direction for cutting and enclosing a piece of target tissue.

An embodiment of a penetration rod 2 is shown in FIG. 1b. It is for penetrating into the body up to the target area. In FIG. 1c a cutting device 4 is shown. It is preferably extendable from the penetration rod 2 and comprises cutting means 5 for cutting off the piece of target tissue from the body. In a preferred embodiment the cutting device 4 is centrally provided inside of the penetration rod 2, although it is also conceivable to arrange the cutting device along the periphery, or anywhere there between, of the penetration rod. In FIG. 1b a cut 10 is shown in the distal end portion 3 of the penetration rod 2. When the cutting device 4 is in its first position it is protected inside of the penetration rod 2 and also the cutting means 5 of the cutting device 4 is protected within the penetration rod 2.

The cutting device 4 is preferably elongated of any cross section, although a circular cross section may be preferable. In its distal end cutting means 5 is provided, which extends radially from the cutting device 4. The cutting means 5 is for cutting off a piece of target tissue to be harvested. The cutting means 5 may have any conceivable shape, such as an L-shape, T-shape, leaf-shape corresponding with the outer shape of the distal end portion 3 of the penetration rod 2, or one or two pin cutters having the shape of the outer shape of the distal end portion 3, for example. The radial distance of the extension of the cutting means 5 corresponds preferably with the radius of the cutting tube 6.

The cutting means 5 could be sharp for mechanical cutting or electrodes for diathermy, for example surgical or monopolar diathermy. If the cutting means 5 is an electrode the cutting device is a connector 8, see FIG. 1c, and insulating means 9 as shown in FIG. 1d is needed.

In FIG. 1e the kit is shown in an assembled way. In the FIG. 1e the cutting tube 6 is extended axially out from the distal end 3 of the penetration rod 2. Also the cutting device 4 is extended axially out from the distal end 3 of the penetration rod 2. The biopsy kit is preferably arranged coaxially around an axis x.

Previously the first position of the cutting device 4 was explained. A second position is when the cutting device 4 is extended shortly out of the penetration rod 2 so that the cutting means 5 is just outside the distal end portion 3 of the penetration rod 2. In this position it is possible to cut during the penetration on its way to the target area. For example, if the penetration rod 2 needs to get through harder tissue as a gland or the like. This is possible both with the embodiment having sharp cutting means 5 and diathermy electrodes as cutting means 5. The advantage of having diathermy electrodes in this case when the penetration rod 2 needs to penetrate harder tissue is that there will be no bleeding.

A third position is when the cutting device 4 is extended so far that it has passed through the piece of target tissue to be harvested and thus can be used to cut off the piece of target tissue at its distal end by means of the cutting means 5. Also this is possible both with the embodiment having sharp cutting means 5 and diathermy electrodes as cutting means 5.

In the vicinity of the distal end of the penetration rod a sealing means may be provided for sealingly fitting with the cutting tube 6. When a withdrawal of the penetration rod 2 is performed a vacuum will be built up in the space that forms between the blunt end of the penetration rod 2 and the distal end of the cutting tube 6. This would facilitate the taking of the biopsy and secure a taken biopsy to remain in the inner tube during withdrawal of the instrument from the body. It is also conceivable to increase the vacuum by having a hole through the penetration rod and connect the penetration rod to a suction pump. Another way is to leave out the sealing means and connect the suction pump to the biopsy taking device.

In order to remove the taken biopsy material, i.e. piece of target tissue, collected inside of the cutting tube the penetration rod may be pushed back into the cutting tube in a distal direction when outside of the body.

It is also conceivable to use an outer tube, too. This will be arranged concentrically outside the cutting tube before the biopsy instrument is penetrated into the body. This outer tube is kept in the penetration channel while the biopsy instrument is removed and thereafter removed. Thus it is possible to minimize the risk of seeding of tumor cells in the penetration channel.

A method of removal of a piece of target tissue from a body is provided, where a biopsy kit 1 is entered into a body through a small skin incision and pushed into a starting position in front of a target tissue area, i.e. when reaching the piece of target tissue to be removed. The biopsy kit 1 comprises at least a penetration rod 2 with preferably a blunt distal end 3, a cutting device 4, and a cutting tube 6.

The blunt penetration rod 2 will separate the tissue while penetrating the body and thus it is possible to move all the way into the position before the biopsy position without cutting tissue. Thus, almost no bleeding will occur and the risk of injuries to the nerves, blood vessels and surrounding tissue will decrease.

Thereafter, the surgeon may choose three different paths to carry out the method. They will be described one by one hereafter. According to a first path the surgeon may withdraw the penetration rod 2 into the cutting tube 6 leaving a space between the distal end of the cutting tube 6 and the distal end of the penetration rod 2, but it is optional.

The surgeon thereafter pushes axially in the distal direction, and preferably rotating back and forth, the cutting tube 6 further into the body cutting with the sharp distal cutting edge 7 so that the piece of target tissue enters into said space and then extending the cutting device 4 axially in the distal direction, which cuts through the piece of target tissue. When the cutting device 4 has passed through the piece of target tissue, and is preferably in line with the distal end of the cutting tube 6, a cutting means 5 of the cutting device 4 is used, preferably rotated, to cut off the piece of target tissue. The piece of target tissue may be cut off within the cutting tube 6 or just outside the cutting edge of the cutting tube 6. Thereafter the biopsy instrument is withdrawn from the body. By pushing the penetration rod 2 forward, when outside of the body, the biopsy material will be pushed out of the cutting tube 6.

According to a second path of carrying out the method, the cutting device 4 is extended through the piece of target tissue. Thereafter, the cutting tube 6 is pushed forward enclosing the piece of target tissue, preferably as far in as the cutting device 4 was extended. Then the cutting means 5 is used to cut off the piece of target tissue. Thereafter the biopsy instrument is withdrawn from the body.

According to a third path of carrying out the method, the cutting device 4 is extended through the piece of target tissue. Thereafter, the cutting means 5 is used, preferably rotated, to cut off the distal end of the piece of target tissue. Then the cutting tube 6 is pushed forward enclosing the piece of target tissue, as far in as the cutting device 4 was extended so that the cutting tube 6 reaches the cut off distal end of the piece of target tissue. Thereafter the biopsy instrument is withdrawn from the body.

In a preferred embodiment the cutting means 5 cuts off the piece of target tissue in its distal end against or in close vicinity to the inside of the distal end portion of the cutting tube 6. It is also conceivable to cut off the tissue just outside of the cutting edge of the cutting tube 6. It is also possible to cut off the piece of target tissue at any position along the inside of the cutting tube 6. The cutting means may cut mechanically or by means of diathermy, preferably while rotating the cutting device 4.

Biopsy kits may be provided in different sizes for different uses. Cutting tube 6 diameters may for example be 2-25 mm, preferably 4-15 mm. When using larger kits it may be possible to not only take a biopsy but at the same time perform the needed surgery. This could be useful in cancer treatment, for example, when a small tumor can be removed directly without the need to first take out a biopsy and analyze it and then perform the surgery. The need of surgery under seduction will be removed. Additionally, it is usually easier to locate the right position when using ultrasonic technology or radiology to identify the position of small tumors compared to when using open surgery. The biopsy kit and the corresponding method would reduce costs for surgery.

The invention claimed is:

1. A biopsy kit for removal of a piece of target tissue from a body, comprising:
    a penetration rod having a distal end portion for penetration into the body,
    a cutting tube having a radius enclosing the penetration rod and comprising circumventing cutting means, the cutting tube being extendable from the distal end portion of the penetration rod for cutting and enclosing the piece of target tissue within the cutting tube, and
    a cutting device centrally provided inside of the penetration rod and extendable distally from the penetration rod, the cutting device comprising distal cutting means rotatable inside the cutting tube for cutting off the piece of target tissue inside the cutting tube when the piece of target tissue is enclosed within the cutting tube, wherein the penetration rod and the cutting device are arranged coaxially along a central axis of the cutting tube, the distal cutting means extending radially outwardly from the central axis for a radial distance corresponding with the radius of the cutting tube, and wherein the cutting device is rotatable around the central axis such that the cutting means rotates inside of the cutting tube in order to be able to cut off the piece of target tissue when the piece of target tissue is positioned inside the cutting tube.

2. The biopsy kit according to claim 1, wherein the distal end portion of the penetration rod is blunt.

3. The biopsy kit according to claim 1, wherein the cutting device is extendable from the penetration rod from a first position, where the cutting means is protected by the penetration rod.

4. The biopsy kit according to claim 1, wherein the cutting device is extendable from the penetration rod from a first position, where the cutting means is protected by the penetration rod, to a second position where the cutting means extends just enough to be able to cut tissue at the distal end portion of the penetration rod.

5. The biopsy kit according to claim 1, wherein the cutting device is extendable from the penetration rod from a position where the cutting means is protected by the penetration rod, to a position where the cutting means extends through the piece of target tissue in order to be able to cut off the piece of target tissue.

6. The biopsy kit according to claim 1, wherein the cutting means is an electrode for diathermy.

7. The biopsy kit according to claim 6, wherein the cutting device is rod shaped and comprises an electrical connector for the electrode.

8. The biopsy kit according to claim 7, wherein the electrical connector is protected by insulating means.

9. The biopsy kit according to claim 1, wherein the cutting tube and/or the cutting device is sealingly fitted to the penetration rod.

10. The biopsy kit according to claim 1, wherein a negative pressure is connected to the biopsy kit.

11. A method of removal of a piece of target tissue from a body using a biopsy kit comprising a penetration rod having a distal end portion for penetration into the body, a cutting tube having a radius enclosing the penetration rod and comprising circumventing cutting means, and a cutting device centrally provided inside of the penetration rod and extendable distally from the penetration rod, wherein the penetration rod and the cutting device are arranged coaxially along a central axis of the cutting tube, the cutting tube being distally extendable from the distal end portion of the penetration rod for cutting and enclosing the piece of target tissue inside the cutting tube, the method comprising the steps of:
    penetrating the tissue of the body using the penetration rod,
    upon reaching the piece of target tissue to be removed, carrying out the following two steps in any consecutive order,
    (i) extending the cutting tube from the penetration rod to cut out and enclose the piece of target tissue,
    (ii) extending the centrally provided cutting device from the penetration rod, the cutting device having a distal cutting means extending radially outwardly from the axis for a radial distance corresponding with the radius of the cutting tube from the penetration rod, to penetrate the piece of target tissue, and additionally,
    cutting off the piece of target tissue, after extending the cutting tube and extending the cutting device, and while the piece of target tissue is enclosed within the cutting tube, by rotating the centrally provided cutting device such that the distal cutting means rotates inside of the cutting tube.

12. The method according to claim 11, comprising providing negative pressure to a biopsy kit.

13. The method according to claim 11, comprising:
   extending the cutting device from the penetration rod from a first position, where the cutting means is protected by the penetration rod, to a second position where the cutting means extends just enough to be able to cut tissue at a distal end portion of the penetration rod, and
   cutting tissue with the cutting means in the second position.

14. A biopsy kit for removal of a piece of target tissue from a body, comprising
   a penetration rod having a distal end portion for penetration into the body,
   a cutting tube having a radius enclosing the penetration rod and comprising circumventing cutting means, the cutting tube being extendable from the distal end portion of the penetration rod for cutting and enclosing the piece of target tissue within the cutting tube, and
   a cutting device centrally provided inside of the penetration rod and distally extendable from the penetration rod, the cutting device comprising distal cutting means rotatable inside the cutting tube for cutting off the piece of target tissue inside the cutting tube when the piece of target tissue is enclosed within the cutting tube,
   wherein the penetration rod and the cutting device are arranged coaxially along a central axis of the cutting tube, with the cutting device centrally disposed, and the distal cutting means extends radially from the central axis for a radial distance corresponding with the radius of the cutting tube, and
   wherein the cutting device is rotatable around the central axis such that the distal cutting means rotates inside of the cutting tube, in order to be able to cut off the piece of tissue when the target tissue is positioned inside the cutting tube, and the distal cutting means is an electrode for diathermy.

* * * * *